(12) United States Patent
Ogawa et al.

(10) Patent No.: US 8,367,860 B2
(45) Date of Patent: Feb. 5, 2013

(54) METHOD FOR PRODUCING (METH) ACRYLIC ACID DERIVITIVE

(75) Inventors: Yasushi Ogawa, Yokkaichi (JP); Shuhei Yada, Tokyo (JP); Yoshiro Suzuki, Yokkaichi (JP); Kenji Takasaki, Yokkaichi (JP); Yukihiro Hasegawa, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 12/127,375

(22) Filed: May 27, 2008

(65) Prior Publication Data

US 2008/0228003 A1 Sep. 18, 2008

Related U.S. Application Data

(63) Continuation of application No. 11/512,321, filed on Aug. 30, 2006, now abandoned, which is a continuation of application No. PCT/JP2004/016679, filed on Nov. 10, 2004.

(30) Foreign Application Priority Data

Apr. 1, 2004 (JP) ................ 2004-109322

(51) Int. Cl.
C07C 69/00 (2006.01)
C07C 69/54 (2006.01)
(52) U.S. Cl. ........................ 560/129; 560/190
(58) Field of Classification Search .......... None
See application file for complete search history.

(56) References Cited

U.S. PATENT DOCUMENTS

| | | | | |
|---|---|---|---|---|
| 2,947,779 A * | 8/1960 | Idol et al. ............ | 560/205 |
| 3,781,332 A | 12/1973 | Sato et al. | |
| 4,012,439 A * | 3/1977 | Erpenbach et al. ...... | 560/205 |
| 4,110,370 A | 8/1978 | Engelbach et al. | |
| 4,199,410 A | 4/1980 | Ohrui et al. | |
| 4,474,981 A | 10/1984 | Katoh et al. | |
| 4,698,440 A * | 10/1987 | Blair et al. .......... | 560/205 |
| 4,873,217 A | 10/1989 | Kawajiri et al. | |
| 4,999,452 A * | 3/1991 | Bunning et al. ........ | 560/208 |
| 6,399,817 B1 * | 6/2002 | Chapman et al. ....... | 562/545 |
| 6,525,216 B1 * | 2/2003 | Nishimura et al. ...... | 562/542 |
| 6,642,414 B2 * | 11/2003 | Mitsumoto et al. ...... | 562/600 |
| 6,713,648 B2 | 3/2004 | Hirao et al. | |
| 6,878,239 B1 | 4/2005 | Matsumoto et al. | |
| 2003/0040570 A1 * | 2/2003 | Nestler et al. ........ | 524/558 |

FOREIGN PATENT DOCUMENTS

| | | |
|---|---|---|
| EP | 1057804 | 12/2000 |
| EP | 1 382 592 A1 | 1/2004 |
| GB | 948687 * | 2/1964 |
| GB | 953763 * | 2/1964 |
| GB | 959880 * | 6/1964 |
| JP | 2000-256221 | 9/2000 |
| JP | 2000-344711 | 12/2000 |
| JP | 2000-351749 | 12/2000 |
| JP | 2001-213839 | 8/2001 |
| SU | 1792344 A3 | 1/1993 |
| WO | WO 99/00354 | 1/1999 |

OTHER PUBLICATIONS

"Safety Guidelines for Handling Acrylic Acid and Acrylates", Japan Acrylate Industry Association, Sixth Edition, Oct. 2002, pp. 20-30, (with English Translation).

Eizou Omori, "Acrylic Acid and Its Polymer," First Edition, Dec. 30, 1973, pp. 14-17, Publisher: Kabushiki Kaisha Shokodo (w/Attached English Abstract).

Kirk-Othmer, Encyclopedia of Chemical Technology, Fourth Edition, vol. 1, 1991, pp. 299-301.

* cited by examiner

*Primary Examiner* — Yate K Cutliff
(74) *Attorney, Agent, or Firm* — Oblon, Spivak, McClelland, Maier & Neustadt, L.L.P.

(57) ABSTRACT

The present invention provides a method for efficiently using an aqueous solution of (meth)acrylic acid at a low concentration formed in a production/storage step of (meth)acrylic acid.

In the present invention, a (meth)acrylic acid derivative is produced by using as a raw material an aqueous solution of (meth)acrylic acid formed by one or both of: a device which reduces a pressure of a gas comprising (meth)acrylic acid in production of (meth)acrylic acid; and a device which collects (meth)acrylic acid from a gas comprising (meth)acrylic acid.

8 Claims, No Drawings

METHOD FOR PRODUCING (METH) ACRYLIC ACID DERIVITIVE

TECHNICAL FIELD

The present invention relates to a method for producing a (meth)acrylic acid derivative. The present invention more specifically relates to a method for using an aqueous solution of (meth)acrylic acid at a low concentration formed in a production step or a process of storage of (meth)acrylic acid, as a material for production of a (meth)acrylic acid derivative (hereinafter, may also be simply referred to as "derivative") without further purification as (meth)acrylic acid.

BACKGROUND ART

A (meth)acrylic acid-containing gas obtained through vapor-phase catalytic oxidation of propane, propylene, isobutene, or (meth)acrolein is collected in water or in a high boiling point solvent, to thereby form a (meth)acrylic acid solution. The (meth)acrylic acid solution is then subjected to a subsequent purification step involving extraction, diffusion, distillation, and crystallization, to thereby purify (meth)acrylic acid.

When a vaporization of (meth)acrylic acid as in distillation is involved in the purification step, an operation is conducted under reduced pressure. This is because reduced pressure decreases an operating temperature to suppress polymerization of (meth)acrylic acid. In addition to an operation of reducing pressure, air or a mixed gas of air and nitrogen (hereinafter, may also be referred to as "mixed gas") may be supplied into a system for suppressing polymerization.

The supplied air or the mixed gas is guided to a vacuum device used for reducing the pressure along with a vapor of (meth)acrylic acid. When a steam ejector is used as the vacuum device, (meth)acrylic acid is trapped in condensed water of a steam discharged from the ejector. When a vacuum pump is used, (meth)acrylic acid is trapped in a seal water thereof.

An example of a technique of recycling the thus-obtained aqueous solution of (meth)acrylic acid includes a method for circulating the aqueous solution to a collecting step of collecting in the above-mentioned water or the high boiling point solvent crude (meth)acrylic acid formed in production of (meth)acrylic acid or to a purification step thereafter (see JP 2000-351749 A, for example). However, in the method, a large volume of water is circulated along with (meth)acrylic acid, and thus, at least energy required for purification of (meth)acrylic acid from the aqueous solution is further increased.

Air or the mixed gas is supplied to (meth)acrylic acid stored in a tank for preventing polymerization. The supplied gas is discharged from the tank as a vent gas along with a vapor of (meth)acrylic acid. (Meth)acrylic acid has a strong odor, and thus is usually guided to a deodorization column and trapped in water or an aqueous solution of caustic soda (see "Safety guidelines for handling acrylic acid and acrylates", 5th edition, Japan Acrylate Industry Association, 1997, for example). The thus-obtained aqueous solution of (meth)acrylic acid has been heretofore treated as waste water. Thus, treatment of the aqueous solution of (meth)acrylic acid has involved a loss of (meth)acrylic acid and an increase in load of waste water treatment.

Meanwhile, JP 2000-351749 A discloses a method for directly introducing a vent gas containing (meth)acrylic acid into the collecting step. However, (meth)acrylic acid is usually produced through a continuous process, and a volume of a vent gas generated from the tank varies depending on receiving or discharge of (meth)acrylic acid. The method may become a variable factor of an operation in a continuous process, and thus is not preferable.

Further, a vent gas from the tank cannot be recycled while a production process of (meth)acrylic acid is stopped, and the vent gas from the tank must be treated separately.

DISCLOSURE OF THE INVENTION

The present invention has been made in view of solving the above problems, and an object of the present invention is therefore to provide a method for efficiently using an aqueous solution of (meth)acrylic acid at a low concentration formed in a production/storage step of (meth)acrylic acid.

The inventors of the present invention have confirmed that concentrations of impurities in an aqueous solution of (meth)acrylic acid at less than 20 mass % formed by trapping in water (meth)acrylic acid vaporized in air or in the mixed gas in a production/storage step of (meth)acrylic acid are substantially lower than that of (meth)acrylic acid.

The inventors of the present invention have conducted intensive studies based on the fact, and have found that (meth)acrylic acid in the aqueous solution can be used as a raw material for the derivative without disposing or circulating to a purification step, that is, purifying (meth)acrylic acid from the aqueous solution of (meth)acrylic acid, and that cooling of the aqueous solution is effective for the use of the aqueous solution. Thus, the inventors of the present invention have completed the present invention.

That is, the present invention is a method for producing a (meth)acrylic acid derivative, which comprises using as a raw material an aqueous solution of (meth)acrylic acid formed by one or both of: a device which reduces a pressure of a gas comprising (meth)acrylic acid in production of (meth)acrylic acid; and a device which collects (meth)acrylic acid from a gas comprising (meth)acrylic acid.

BEST MODE FOR CARRYING OUT THE INVENTION

In the present invention, a (meth)acrylic acid derivative is produced by using as a raw material an aqueous solution of (meth)acrylic acid formed by one or both of: a device which reduces a pressure of a gas comprising (meth)acrylic acid in production of (meth)acrylic acid; and a device which collects (meth)acrylic acid from a gas comprising (meth)acrylic acid. The term "(meth)acrylic acid " refers to acrylic acid or methacrylic acid. Further, the phrase "an aqueous solution of (meth)acrylic acid" refers to an aqueous solution of (meth) acrylic acid formed by trapping in water (meth)acrylic acid vaporized along with air or a mixed gas of air and nitrogen used in a production and storage step of (meth)acrylic acid.

A known device for reducing a gas pressure can be used for the device which reduces a pressure of a gas. Examples thereof include: a kinetic vacuum pump such as a steam ejector involving gas transportation by an entrainment effect of a working fluid (steam) blowing at high speed; and a liquid ring pump such as a normal vacuum pump involving sealing of a liquid (water) by discharging air in a casing.

Examples of the aqueous solution of (meth)acrylic acid formed by the device which reduces a pressure of a gas include: a condensed water of a vapor used for a steam ejector; and a seal water of a vacuum pump.

A known device for collecting a predetermined component in a gas can be used for the device which collects (meth) acrylic acid. An example thereof includes a deodorization device for collecting in water (meth)acrylic acid from a gas to deodorize the gas such as a packed column, a plate column, a spray column, and a scrubber.

An example of the aqueous solution of (meth)acrylic acid formed in the deodorization device includes a water used for collecting (meth)acrylic acid in the deodorization device.

The above-mentioned aqueous solution of (meth)acrylic acid may be used alone or may be used as a mixture of a plurality thereof.

In the present invention, a (meth)acrylic acid content in the aqueous solution of (meth)acrylic acid is not particularly limited, but is preferably less than 20 mass % from a viewpoint of preventing occurrence of polymerization of (meth) acrylic acid in the aqueous solution. The content can be adjusted by mixing of the above-mentioned aqueous solution of (meth)acrylic acid or dilution with water.

In the present invention, a stainless pipe is preferably used as a pipe for passing the aqueous solution of (meth)acrylic acid from the viewpoint of preventing rust formation in the aqueous solution of (meth)acrylic acid.

In the present invention, measures to suppress an occurrence of polymerization are preferably devised from the viewpoint of preventing polymerization of (meth)acrylic acid in the aqueous solution of (meth)acrylic acid. Examples of the measures which may be employed in the present invention include a method for supplying a polymerization inhibitor to the device which reduces a pressure of a gas as disclosed in JP 2000-344711 A and a method for cooling the aqueous solution of (meth)acrylic acid.

The method for supplying a polymerization inhibitor as disclosed in the bulletin is effective for preventing polymerization of (meth)acrylic acid alone. However, the method is not effective for preventing formation of an acrylic acid dimer through a dimerization reaction of acrylic acid or formation of hydroxypropionic acid or hydroxybutanoic acid through water addition to (meth)acrylic acid, and concentrations of the impurities may increase.

The method for cooling the aqueous solution of (meth) acrylic acid is preferable from the viewpoints of preventing occurrence of polymerization of (meth)acrylic acid in the aqueous solution and suppressing formation or increase of the above-mentioned impurities. Further, the method for cooling the aqueous solution of (meth)acrylic acid is preferable from the viewpoint of preventing occurrence of polymerization of (meth)acrylic acid in the aqueous solution in a case of production of super absorbent polymers or the like in which a reaction in following production of a derivative is inhibited by the polymerization inhibitor.

In the present invention, a temperature of the aqueous solution of (meth)acrylic acid is not particularly limited, but is preferably lower than 40° C. The temperature can be adjusted by indirect cooling or indirect heating with a heat exchanger, cooling by supply of water, or the like.

Hereinafter, the aqueous solution of (meth)acrylic acid formed by each device will be described in more detail.

<Steam Ejector>

In the steam ejector used for reducing a pressure of a distillation column or flasher used for vaporization of a liquid, a vapor used for reducing the pressure is discharged along with sucked air or the mixed gas, and (meth)acrylic acid. The vapor discharged from the ejector is usually cooled for the purpose of condensation alone, and thus, a temperature of the condensed water is about 45 to 55° C. To suppress polymerization of (meth)acrylic acid in the aqueous solution of (meth) acrylic acid and increase of impurities, adjusting a temperature of the aqueous solution to lower than 40° C. is effective.

<Vacuum Pump>

In a Seal water used for the vacuum pump, (meth)acrylic acid entraining with the sucked air or the mixed gas is trapped. A high concentration of (meth)acrylic acid in the water easily causes polymerization, and thus, the seal water is preferably sufficiently supplied. A (meth)acrylic acid concentration in the water is preferably less than 20 mass %, more preferably less than 10 mass %. A temperature of the water is preferably maintained lower than 40° C. for suppressing polymerization and formation of impurities as in the case of the condensed water from the ejector.

<Deodorization Device>

Air or the mixed gas supplied to a storage tank for (meth) acrylic acid is discharged from the tank as a vent gas containing a vapor of (meth)acrylic acid. The vent gas is then guided into the deodorization device, and (meth)acrylic acid in the gas is trapped in water in the device. In order to prevent leak of the vent gas to the atmosphere before (meth)acrylic acid is trapped, (meth)acrylic acid in the vent gas may be forcibly trapped in water by a scrubber or the like and this water may be supplied to the deodorization device. In order to suppress polymerization and formation of impurities, and to substantially reduce a concentration of untrapped (meth)acrylic acid, a (meth)acrylic acid concentration in water used for trapping is preferably less than 10 mass % and a temperature of the water is preferably lower than 40° C.

In the production step of (meth)acrylic acid, when a dry-type vacuum pump not requiring water for an operation of the pump is used, part of (meth)acrylic acid is condensed and liquefied at an outlet of the pump. However, the remaining (meth)acrylic acid is included as a gas in an exhaust gas. (Meth)acrylic acid in the exhaust gas is trapped in the same manner as the vent gas from the storage tank. The liquefied (meth)acrylic acid is in high concentration, and thus is easily polymerized. Thus, a solvent such as water, preferably a solvent containing a polymerization inhibitor may be supplied to the outlet of the pump or the like. In this case, (meth)acrylic acid is trapped in the solvent supplied to the outlet of the pump, to thereby form a (meth)acrylic acid solution (mainly aqueous solution). The thus-obtained (meth) acrylic acid solution may be also an object of the present invention.

The aqueous solution of (meth)acrylic acid obtained through the above-mentioned method may be directly supplied to a step for producing the derivative, or may be stored in a drum or a tank once. A temperature of the aqueous solution during storage is preferably lower than 40° C., more preferably lower than 30° C. A temperature of the aqueous solution of (meth)acrylic acid during storage is not particularly limited so long as the aqueous solution of (meth)acrylic acid can maintain a liquid state, and is determined depending on a freezing point of the aqueous solution of (meth)acrylic acid. The freezing point of the aqueous solution of (meth) acrylic acid is determined depending on a water content in the aqueous solution of (meth)acrylic acid. For example, a freezing point of the aqueous solution of acrylic acid is 5.5° C. when a water content is 5 mass % and −10.3° C. when a water content is 30 mass %.

In the present invention, at least one filter is preferably provided at a position where the aqueous solution of (meth) acrylic acid is supplied from the device which traps (meth) acrylic acid in the gas in water to a device for producing the derivative from the viewpoint of removing polymerized products, impurities, and solid products such as rust in the aqueous solution of (meth)acrylic acid. The filter to be used is not particularly limited, and a wire gauze or a resin hollow fiber membrane can be used as the filter, for example. The filter is preferably used in a mode allowing change or washing of the filter without stopping the operation of the process. A specific example of the mode is any one of: a mode having a bypass line; a mode in which a plurality of filters are provided in parallel; and a mode having a line for washing.

In the present invention, a (meth)acrylic acid concentration in the aqueous solution of (meth)acrylic acid is preferably measured before the aqueous solution of (meth)acrylic acid is supplied to the step for producing the derivative. A method for measuring the concentration is not particularly limited, but the use of neutralization titration or gas chromatography is effective. The measurement of the concentration may be also automatically conducted in online.

In the present invention, a (meth)acrylic acid derivative is produced by using the aqueous solution of (meth)acrylic acid as a raw material. The derivative to be produced is not particularly limited so long as the derivative is a compound produced from the aqueous solution of (meth)acrylic acid. Examples of the derivative include (meth)acrylate and a polymerized product such as a homopolymer or a copolymer comprising (meth)acrylic acid as a monomer.

The aqueous solution of (meth)acrylic acid may be supplied to the step for producing the derivative alone or may be combined with (meth)acrylic acid not in the aqueous solution of (meth)acrylic acid or a composition containing the same such as purified (meth)acrylic acid and (meth)acrylic acid from another plant. The aqueous solution may be supplied to the device for producing the derivative from 1 supply position or from 2 or more supply positions. When purified (meth)acrylic acid is combined, a supply position of the aqueous solution of (meth)acrylic acid and a supply position of the purified (meth)acrylic acid may be the same or different from each other.

As described above, the aqueous solution of (meth)acrylic acid obtained from the production step and/or storage step of (meth)acrylic acid is supplied to the step for producing the derivative, to thereby allow reduction in loss of (meth)acrylic acid and reduction in volume of waste water treatment even when production of (meth)acrylic acid is stopped.

EXAMPLES

Hereinafter, the present invention will be described in more detail based on examples, but the present invention is not limited thereto.
<Preparation of Aqueous Solution of Acrylic Acid>

An aqueous solution of acrylic acid used in the present examples was obtained through the following procedure.

The aqueous solution of acrylic acid used in the present examples was obtained during purification through distillation of acrylic acid produced through a vapor-phase catalytic reaction and during storage of purified acrylic acid. A purification through distillation of acrylic acid comprises: a distillation column; a condenser for cooling a vapor of acrylic acid distilled from the distillation column; a reflux tank for receiving acrylic acid condensed in the condenser; a vent gas condenser for further cooling a gas component in the reflux tank; and a steam ejector for bringing a distillation atmosphere under reduced pressure.

A pump is connected to the reflux tank, and a pipe connected to a top of the distillation column is connected to the pump. Another pipe branches from this pipe. Part of acrylic acid received in the reflux tank is returned to the distillation column, and part thereof is received as purified acrylic acid in a tank for storage.

Meanwhile, a vent gas discharged from the steam ejector and a gas in the tank were supplied to a deodorization device provided with: a vessel for receiving water; and an introduction pipe for introducing the gas into the water received in the vessel. In the deodorization device, an aqueous solution is drawn and water was supplied, to thereby adjust an acrylic acid concentration in the aqueous solution in the vessel within a predetermined range.

An aqueous solution of acrylic acid having an acrylic acid concentration of 3 mass % was prepared by: collecting a condensed liquid of a steam used for reducing a pressure of the distillation atmosphere in the steam ejector; mixing the aqueous solution drawn from the deodorization device; and further adding water as required.

Example 1

Acrylate was produced by using the prepared aqueous solution of acrylic acid and purified acrylic acid as raw materials. A constitution of a production device used for production of acrylate is described below.

The production device for producing acrylate is provided with: a reactor; a distillation column connected to an upper part of the reactor; a condenser for cooling a vapor of azeotropic mixture distilled from the distillation column; a separation tank for receiving the azeotropic mixture condensed in the condenser and separating the mixture into a water phase and an oil phase; a reaction liquid circulation line for drawing a liquid in the reactor from the reactor and supplying the liquid into the distillation column; and a first take out line for taking out part of the liquid in the reaction liquid circulation line.

The separation tank comprises: a water phase draw line; and a reflux line for an oil phase for returning the oil phase separated in the separation tank to the distillation column. A second take out line which branches from the reflux line for an oil phase is connected to the reflux line for an oil phase, and is used as required.

3,000 kg of purified acrylic acid, 4,036 kg of n-butyl alcohol, 1.4 kg of hydroquinone as a polymerization inhibitor, and 70 kg of p-toluenesulfonic acid as a catalyst were dissolved in 675 kg of a 3 mass % aqueous solution of acrylic acid prepared in advance. Then, the solution was supplied to the reactor in the production device.

While the reaction liquid containing the raw materials and products was circulated by the reaction liquid circulation line, a reaction was continued. A vapor distilled from the top part of the distillation column was condensed in the condenser, and the obtained condensed liquid was received in the separation tank.

The oil phase in the separation tank partially contained the formed butyl acrylate. However, the oil phase contained much n-butyl alcohol which is a raw material, and thus was supplied to the reactor as part of a raw material for an esterification reaction in the reactor through the reflux line for an oil phase, to thereby maintain a constant volume of the oil phase in the separation tank. Meanwhile, the water phase in the separation column was continuously drawn out of the system so that a constant water volume of the water phase was maintained.

The reaction liquid was analyzed by gas chromatography to observe an acrylic acid conversion rate. When the conversion rate reached 99%, heating was stopped. The obtained reaction liquid was taken out from the first take out line through the reaction liquid circulation line. The taken-out reaction liquid was washed with water and an aqueous solution of sodium hydroxide, and then supplied as crude butyl acrylate to a distillation step for purification.

In the distillation step, the crude butyl acrylate was distilled, to thereby obtain purified butyl acrylate. Purity determination of the obtained purified butyl acrylate or quantitative determination of the impurities was conducted. The result revealed that the purified butyl acrylate has the same quality as that of butyl acrylate obtained through the esterification reaction using purified acrylic acid for acrylic acid as a raw material.

Example 2

The prepared aqueous solution of acrylic acid, purified acrylic acid, and water were mixed, to thereby prepare an aqueous solution of acrylic acid having a concentration of 75 mass %. While the aqueous solution of acrylic acid was cooled, a 25 mass % aqueous solution of sodium hydroxide was added to neutralize 80% of acrylic acid. Ethylene glycol diglycidyl ether (DENACOL EX810, available from Nagase ChemteX Corporation), sodium hypophosphite monohydrate, and potassium persulfate were added to and dissolved in the solution, to thereby prepare an aqueous monomer solution.

To the thus-prepared aqueous monomer solution, polyoxyethylene octyl phenyl ether phosphate (PLYSURF (a trademark of Dai-ichi Kogyo Seiyaku Co., Ltd.) A210G, available from Dai-ichi Kogyo Seiyaku Co., Ltd., an average polymerization degree of an oxyethylene group of about 7) and cyclohexane were added, and the aqueous monomer solution was emulsified at 15,000 revolutions for 3 minutes using a mechanical emulsifier (Physcotron, manufactured by Nition Irika Kikai Seisakusyo Co., Ltd.), to thereby prepare an emulsified monomer liquid.

Cyclohexane was placed in a four-necked round-bottomed flask equipped with a stirrer, a reflux condenser, a thermometer, and a nitrogen gas introduction pipe. To the resultant, polyoxyethylene octyl phenyl ether phosphate (PLYSURF (a trademark of Dai-ichi Kogyo Seiyaku Co., Ltd.) A210G, available from Dai-ichi Kogyo Seiyaku Co., Ltd., an average polymerization degree of an oxyethylene group of about 7) was added, and the mixture was stirred at 420 rpm for dispersion. After an atmosphere inside the flask was replaced with nitrogen, the flask was heated to 80° C. for refluxing cyclohexane. Part of the emulsified monomer liquid was dropped into the flask. After the dropping was completed, the resultant was left at stand for 10 minutes at the same temperature, and the remaining aqueous monomer solution was dropped thereinto. After the dropping was completed, the resultant was maintained at 75° C. for 30 minutes and dehydrated until a water content in resin particles formed through azeotropy with cyclohexane reached 7%.

After the dehydration was completed, stirring was stopped. Resin particles in which the resin particles were settled at the bottom of the flask and cyclohexane were separated through decantation. The obtained resin particles were heated to 90° C. to remove cyclohexane and slight water adhered thereon, to thereby obtain super absorbent polymers.

Properties of the super absorbent polymers such as water absorbing ability, a pressured absorption rate, an average particle size, a bulk density, and fixability of the absorbent polymers were measured. The results confirmed that the super absorbent polymers have the same properties as those of a super absorbent polymers similarly produced by using the purified acrylic acid alone.

INDUSTRIAL APPLICABILITY

According to the present invention, loss of (meth)acrylic acid in the production step and/or storage step of (meth) acrylic acid and a volume of waste water treatment can be reduced.

The invention claimed is:

1. A method for producing a (meth)acrylic acid derivative selected from (meth)acrylate or a polymerized product of (meth)acrylic acid, comprising
reacting (meth)acrylic acid with an alcohol or polymerizing (meth)acrylic acid using as a raw material an aqueous solution of (meth)acrylic acid without further purification to produce a (meth)acrylic acid derivative,
wherein the aqueous solution of (meth)acrylic acid is formed in a production/storage step of (meth)acrylic acid and comprises at least one selected from the group consisting of:
(1) a condensed water of a vapor used for a steam ejector;
(2) a seal water of a vacuum pump; and
(3) a water used for collecting (meth)acrylic acid in a deodorization device for collecting (meth)acrylic acid from a gas to deodorize the gas; and
wherein the aqueous solution of (meth)acrylic acid and purified (meth)acrylic acid are used as the raw materials.

2. The method for producing a (meth)acrylic acid derivative according to claim 1, wherein at least one selected from the group consisting of:
the condensed water of a vapor used for a steam ejector, the seal water of a vacuum pump, and the water used for collecting (meth)acrylic acid in the deodorization device; is cooled to lower than 40° C., or diluted with water, or subjected to both the cooling and the dilution operations to be used as the raw material.

3. The method for producing a (meth)acrylic acid derivative according to claim 1, wherein the aqueous solution of (meth)acrylic acid has a (meth)acrylic acid content of less than 20 mass%.

4. The method for producing a (meth)acrylic acid derivative according to claim 1, comprising reacting (meth)acrylic acid with an alcohol.

5. The method for producing a (meth)acrylic acid derivative according to claim 1, comprising polymerizing (meth) acrylic acid.

6. The method for producing a (meth)acrylic acid derivative according to claim 1, wherein the aqueous solution of (meth)acrylic acid comprises a condensed water of a vapor used for a steam ejector.

7. The method for producing a (meth)acrylic acid derivative according to claim 1, wherein the aqueous solution of (meth)acrylic acid comprises a seal water of a vacuum pump.

8. The method for producing a (meth)acrylic acid derivative according to claim 1, wherein the aqueous solution of (meth)acrylic acid comprises a water used for collecting (meth)acrylic acid in a deodorization device for collecting (meth)acrylic acid from a gas to deodorize the gas.

* * * * *